(12) United States Patent
Eng

(10) Patent No.: US 7,358,211 B2
(45) Date of Patent: Apr. 15, 2008

(54) CATALYST FOR THE PRODUCTION OF 1,3-PROPANEDIOL BY CATALYTIC HYDROGENATION OF 3-HYDROXYPROPANAL

(75) Inventor: John Harvey Eng, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 150 days.

(21) Appl. No.: 10/996,756

(22) Filed: Nov. 24, 2004

(65) Prior Publication Data

US 2006/0111595 A1    May 25, 2006

(51) Int. Cl.
  *B01J 23/40* (2006.01)
  *B01J 23/42* (2006.01)
  *B01J 23/00* (2006.01)
(52) U.S. Cl. ..................... 502/326; 502/350
(58) Field of Classification Search ............. 502/326, 502/350
  See application file for complete search history.

(56) References Cited

U.S. PATENT DOCUMENTS

| | | | | |
|---|---|---|---|---|
| 4,711,871 A | * | 12/1987 | Wachs et al. | ........... 502/325 |
| 4,822,824 A | * | 4/1989 | Iglesia et al. | ........... 518/709 |
| 4,861,747 A | * | 8/1989 | Wachs et al. | ........... 502/325 |
| 5,015,789 A | | 5/1991 | Arntz et al. | |
| 5,171,898 A | | 12/1992 | Arntz et al. | |
| 5,276,201 A | | 1/1994 | Haas et al. | |
| 5,284,979 A | | 2/1994 | Haas et al. | |
| 5,334,778 A | | 8/1994 | Haas et al. | |
| 5,364,984 A | | 11/1994 | Arntz et al. | |
| 5,364,987 A | | 11/1994 | Haas et al. | |
| 5,686,378 A | * | 11/1997 | Katamoto | ........... 502/338 |
| 5,712,331 A | * | 1/1998 | Ryang | ........... 523/400 |
| 5,908,607 A | * | 6/1999 | Abekawa et al. | ........... 423/502 |
| 5,962,745 A | | 10/1999 | Brossmer et al. | |
| 6,111,135 A | | 8/2000 | Adelman et al. | |
| 6,124,367 A | * | 9/2000 | Plecha et al. | ........... 518/715 |
| 6,140,543 A | | 10/2000 | Brossmer et al. | |
| 6,191,067 B1 | * | 2/2001 | Koike et al. | ........... 502/350 |
| 6,232,511 B1 | | 5/2001 | Haas et al. | |
| 6,235,677 B1 | * | 5/2001 | Manzer et al. | ........... 502/232 |
| 6,235,948 B1 | | 5/2001 | Sunkara et al. | |
| 6,277,346 B1 | * | 8/2001 | Murasawa et al. | ....... 423/239.2 |

(Continued)

OTHER PUBLICATIONS

Kirk-Othmer Encyclopedia of Chemical Technology, Third Edition (1982), vol. 19, pp. 880-914.

(Continued)

*Primary Examiner*—Cam N. Nguyen

(57) ABSTRACT

A process for preparing a catalyst, comprising sequentially: (a) saturating a $TiO_2$ support with aqueous ruthenium solution; (b) treating the ruthenium saturated $TiO_2$ support with an aqueous base solution; and (c) curing the ruthenium saturated $TiO_2$ to impregnate the $TiO_2$ with ruthenium. Preferably, subsequent to step (c) the process comprises sequentially (d) washing the ruthenium impregnated $TiO_2$ with water, (e) drying the washed ruthenium impregnated $TiO_2$, and (f) heat treating the ruthenium impregnated $TiO_2$ under reducing conditions at temperatures of 150-800° C. A catalyst prepared by the process. A process for the production of 1,3-propanediol, comprising: (a) providing 3-hydroxypropanal and the catalyst, and (b) hydrogenating the 3-hydroxypropanal in the presence of the catalyst.

17 Claims, 4 Drawing Sheets

U.S. PATENT DOCUMENTS

| | | |
|---|---|---|
| 6,284,930 B1 | 9/2001 | Haas et al. |
| 6,342,646 B1 | 1/2002 | Haas et al. |
| 6,673,739 B2 * | 1/2004 | Yamazaki et al. .......... 502/216 |
| 6,693,222 B2 | 2/2004 | Haas et al. |
| 6,743,749 B2 * | 6/2004 | Morikawa et al. .......... 502/349 |
| 6,852,667 B2 * | 2/2005 | Hibi et al. .................. 502/325 |
| 6,958,309 B2 * | 10/2005 | Wang et al. ................ 502/325 |
| 6,992,040 B2 * | 1/2006 | Muller et al. ............... 502/327 |
| 2003/0144130 A1 * | 7/2003 | Clark et al. .................. 502/38 |

OTHER PUBLICATIONS

Johnson Matthey Heterogeneous Catalysis Technical Guide, p. 4.
Degussa Fixed Bed Catalysts Brochure, p. 2.

* cited by examiner

US 7,358,211 B2

CATALYST FOR THE PRODUCTION OF 1,3-PROPANEDIOL BY CATALYTIC HYDROGENATION OF 3-HYDROXYPROPANAL

FIELD OF THE INVENTION

This invention concerns catalysts comprising ruthenium supported on titanium dioxide, their production, and their use in production of 1,3-propanediol (PDO) by catalytic hydrogenation of 3-hydroxypropanal (HPA).

TECHNICAL BACKGROUND OF THE INVENTION 1,3-Propanediol (PDO) is used as a monomer unit for polyesters and polyurethanes and as a starting material for synthesizing cyclic compounds.

Various processes are known for the production of PDO via 3-hydroxypropanal (HPA) which start either from $C_2$ and $C_1$ structural units or from a $C_3$ structural unit, such as, for example, acrolein. When acrolein is used, it is first hydrated in aqueous phase in the presence of an acidic catalyst to form HPA. After removing the unreacted acrolein, the aqueous reaction mixture formed during hydration still contains, in addition to 85 weight %, based on total organics, of HPA, approximately 8 weight % 4-oxaheptane-1,7-dial and further organic components in smaller proportions by weight. This reaction mixture is hydrogenated in the presence of hydrogenation catalysts to produce PDO. The PDO is recovered from the reaction mixture by distillation and/or extraction based methods known to those skilled in the art.

This invention resulted from the desire for an improved hydrogenation process for the conversion of 3-hydroxypropanal (HPA) to 1,3-propanediol (PDO) in the presence of a $TiO_2$ supported ruthenium catalyst.

Hydrogenation processes may be characterized by the percent conversions of starting material to desired product, selectivities, and space-time yields achievable therewith. Percent conversion of HPA to PDO is defined by:

$$X = \% \text{ Conversion to } PDO = \frac{\text{moles of } PDO \text{ formed}}{\text{moles of } HPA \text{ supplied}} \times 100$$

Selectivity of the hydrogenation process is a measure of the amount of converted HPA which is converted into the desired product:

$$\% \text{ Selectivity} = \frac{\text{moles of } PDO \text{ formed}}{\text{moles of } HPA \text{ converted}} \times 100$$

The space-time yield is another important characteristic for continuous hydrogenation processes, stating the achievable quantity of product per unit time and reaction volume.

When hydrogenating HPA to PDO on a large industrial scale, it is vital, with regard to the economic viability of the hydrogenation process and the quality of the product, for conversion to PDO and selectivity to be as close as possible to 100%. The PDO may be separated from the aqueous reaction media as well as from remaining HPA and secondary products contained in the product stream by distillation after the hydrogenation. However, this distillative separation is rendered very difficult by residual HPA and secondary products and may even become impossible due to reactions between the residual HPA and PDO to yield acetals, such as 2-(2'-hydroxyethyl)-1,3-dioxane (HED), which have a boiling point close to the boiling point of PDO. Thus, the lower the conversion and selectivity, the poorer the achievable product quality. Product streams containing excessive amounts of HED may be treated in a cleanup hydrogenation reactor to lower the HED level. Such post-treatment adds cost and investment. Thus, a catalyst that offers reduced HED levels offers significant economic advantage.

In order to produce PDO economically, it is also important for the catalyst to exhibit high activity for the hydrogenation of FPA. It is desirable to find a process which minimizes the quantity of catalyst required for the production of PDO.

Another important criterion for hydrogenation catalysts is their operational service life. Good catalysts lead to high conversion and high selectivity in the hydrogenation of HPA to PDO over an extended service life.

Conversion, selectivity, and space-time yield are influenced by the characteristics of the catalyst and by the hydrogenation conditions, such as reaction temperature, hydrogen pressure and duration of hydrogenation or, in the case of continuous hydrogenation, by the liquid hourly space velocity (LHSV).

U.S. Pat. No. 5,334,778 discloses a two-stage process for hydrogenating HPA which yields PDO having a residual carbonyl content, expressed as propanal, of below 500 ppm. The hydrogenation is carried out at 30° C. to 80° C. to a HPA conversion of 50 to 95% and then is continued at 100° C. to 180° C. to a HPA conversion of substantially 100%. Suitable hydrogenation catalysts therein include Raney nickel suspension catalysts, and supported catalysts based on platinum or ruthenium on activated carbon, $Al_2O_3$, $SiO_2$, or $TiO_2$ as well as nickel on oxide- or silicate-containing supports.

According to U.S. Pat. No. 5,015,789, very active nickel catalysts exhibit inadequate long-term stability, with a rapid drop in hydrogenation conversion and reaction speed upon repeated use of the catalyst. This results in frequent replacement of the entire catalyst packing, which is associated with known problems in the disposal and working up of compounds containing nickel. In addition, soluble nickel compounds can form and are released into the product stream, requiring further steps to separate the resulting contaminants.

U.S. Pat. No. 5,364,984 discloses a process for preparing PDO from HPA in an aqueous solution using a catalyst formed principally of titanium dioxide on which platinum is applied in a finely divided form. Preferred is a pyrogenic titanium dioxide obtained from titanium tetrachloride by flame hydrolysis, such as P25 (Degussa-Huils AG, Frankfurt am Main, Germany), presently available as Aeroxide® $TiO_2$ P25 (Degussa Corporation, Piscataway, N.J.). The pyrogenic titanium dioxide is processed into shaped particles such as pellets, granulates, or extrusion molded particles and is then impregnated with the platinum, preferably using a soluble platinum compound such as hexachloroplatinic acid, and subsequently dried and reduced in a stream of hydrogen for 1 to 10 hours at temperatures of 250 to 500° C.

U.S. Pat. No. 6,232,511 B1 discloses a process for the production of PDO by the heterogeneously catalyzed hydrogenation of HPA. The catalyst is a supported catalyst which consists of an oxide phase, and on which is present ruthenium. The oxide phase may be $TiO_2$, $SiO_2$, $Al_2O_3$ and/or the mixed oxide thereof, such as aluminum silicate; MgO, zeolites and/or zirconium dioxide; or mixtures of oxide phases. Preferred oxide phases suitable as support materials include $TiO_2$ and $SiO_2$. The titanium dioxide ($TiO_2$) used may be a pyrogenically produced titanium dioxide, such as Aeroxide® $TiO_2$ P25 (Degussa Corporation, Piscataway, N.J.). The oxide phase may be coated by means of the incipient wetness method whereby the support is loaded with an aqueous ruthenium chloride solution, the loaded support is dried preferably at 20 to 100° C. in an inert gas atmosphere, and the dried impregnated support is then reduced with hydrogen to form metallic ruthenium, preferably at a temperature of 100 to 500° C. for a period of 20 minutes to 24 hours. The examples show preparation of a catalyst by reducing with a hydrogen at 200° C. for 8 hours a ruthenium impregnated titanium dioxide Aeroxide® $TiO_2$ P25 (Degussa Corporation, Piscataway, N.J.) support.

There is still a need for a catalyst with: (a) excellent activity, (b) better catalyst selectivity—particularly lower 2-(2'-hydroxyethyl)-1,3-dioxane (HED) formation, (c) improved stability—longer lifetime in making PDO, and (c) improved ruthenium dispersion, enabling excellent activity, selectivity and stability with lower levels of ruthenium.

SUMMARY OF THE INVENTION

This invention is directed to a process for preparing a catalyst, comprising sequentially: (a) saturating a $TiO_2$ support with aqueous ruthenium solution; (b) treating the ruthenium saturated $TiO_2$ support with an aqueous base solution; and (c) curing the ruthenium saturated $TiO_2$ to impregnate the $TiO_2$ with ruthenium. Preferably, subsequent to step (c) the process comprises sequentially (d) washing the ruthenium impregnated $TiO_2$ with water, (e) drying the washed ruthenium impregnated $TiO_2$, and (f) heat treating the ruthenium impregnated $TiO_2$ under reducing conditions at temperatures of 150-800° C. In addition, the invention is directed to catalysts prepared by the process. The invention is also directed to a catalyst prepared by the process.

The invention is further directed to a process for the production of 1,3-propanediol, comprising: (a) providing 3-hydroxypropanal and the catalyst, and (b) hydrogenating the 3-hydroxypropanal in the presence of the catalyst. The process of the present invention, utilizing the catalysts of the present invention, offers improvement in activity, selectivity and stability (longer lifetime) over known processes. The process of the present invention yields a product stream containing less than 1% HED, measured as described below, at 3-hydroxypropanal conversions of greater than or equal to 90%, preferably greater than or equal to 95% conversion and, most preferably, greater than or equal to 99% conversion.

DETAILED DESCRIPTION OF THE INVENTION

Figure 1:
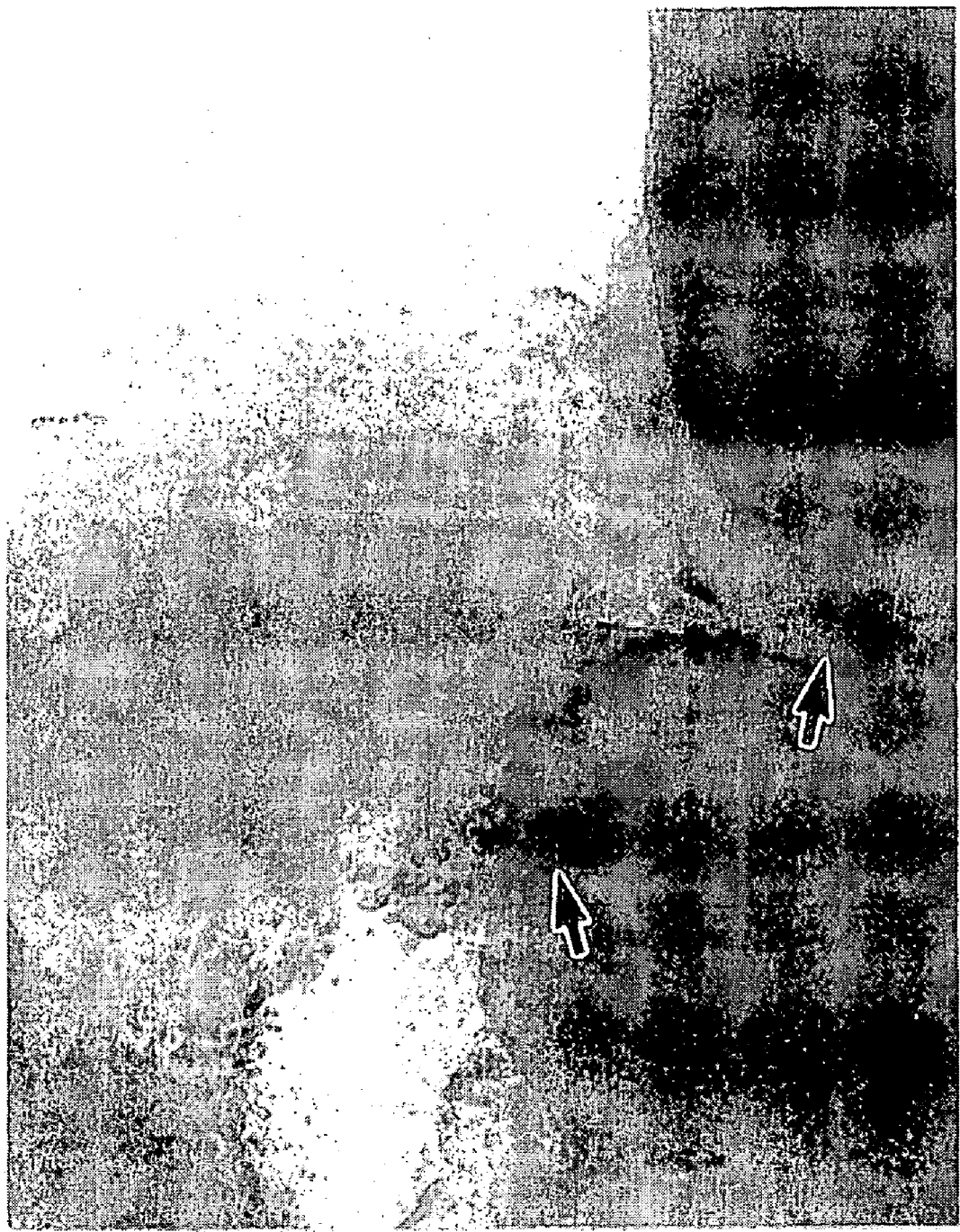
FIG. 1 is a photomicrograph of a ruthenium/$TiO_2$ catalyst corresponding to comparative example 4.

All patents, patent applications, and publications referred to in this document are incorporated herein by reference in their entirety.

Unless stated otherwise, all percentages, parts, ratios, etc., are by weight. Further, when an amount, concentration, or other value or parameter is given as either a range, preferred range or a list of upper preferable values and lower preferable values, the recited amount, concentration, or other value or parameter is intended to include all ranges formed from any pair of any upper range limit or preferred value and any lower range limit or preferred value, regardless of whether such ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The catalysts of the present invention are $TiO_2$ supported ruthenium hydrogenation catalysts, such as those described and prepared by the process described in U.S. Pat. No. 6,232,511 B1, and differ from previously known catalysts in that they are treated with an alkaline solution or a base (e.g., NaOH) to a specified pH during deposition of ruthenium on the $TiO_2$ support. Except with respect to the base treatment and the wider temperature range described for heat treatment, the catalysts and processes are basically the same as those described and prepared by the process described in U.S. Pat. No. 6,232,511 B1.

Preferably the catalyst consists essentially of ruthenium on a $TiO_2$ support. Preferably the catalyst comprises or consists essentially of $TiO_2$ and 0.1 to 20 weight %, more preferably up to 10 weight %, and most preferably up to 5 weight %, of the ruthenium (as metal), by weight of the catalyst.

The catalysts of this invention are heterogeneous, i.e., they are solid catalysts while reaction occurs in a liquid phase, particularly during the preparation of PDO described herein.

Titanium dioxide catalysts supports of the type described in the art can be used in the invention.

The titanium dioxide ($TiO_2$) used as starting material for the preparation of the catalysts of the present invention is preferably a pyrogenically produced titanium dioxide, particularly titanium dioxide produced by flame hydrolysis of titanium tetrachloride. The pyrogenic titanium dioxide used may, for example, be characterized as having a BET surface area of 40 to 60 $m^2/g$, a total pore volume of 0.25 to 0.75 ml/g, an average primary particle size of 20 nm, a density of 3.7 $g/cm^3$ and a structure as determined by x-ray corresponding to 20 to 40% rutile and 80 to 60% anatase. Such pyrogenic titanium dioxide is typically contaminated with less than 0.5 weight % of silicon dioxide, aluminum oxide, and iron oxide.

Pyrogenic $TiO_2$, such as Aeroxide® $TiO_2$ P25 (Degussa Corporation, Piscataway, N.J.), is particularly suitable as a support for the catalytically active component, and has a BET surface area of, on average, 50 $m^2/g$.

The titanium dioxide support may be thermally treated (annealed) prior to use, and such as treatment is preferred with the pyrogenically produced titanium dioxide supports. Calcination (defined herein as heat treatment in air or other inert gas (e.g, nitrogen)) at 550-900° C., preferably at about 800° C., is an example of such a thermal treatment. Calcination decreases the surface area and, with supports that are not 100% rutile phase, normally increases the percentage of rutile phase. X-ray diffraction analysis of such a thermally treated, pyrogenically produced titanium dioxide showed a rutile content of 99%, as opposed to a rutile content of 19% for the material before thermal treatment.

Anatase 99.9%, such as those commercially available from Aldrich (Milwaukee, Wis.), may also be employed as starting material for the catalysts of the present invention.

The titanium dioxide may be shaped into moldings such as, for example, pellets, granules, or extrudates using methods known in the art, such as those described in U.S. Pat. No. 5,364,984.

The ruthenium solutions useful in the present invention are any compounds that are water-soluble or can be readily converted to a water-soluble or partially water-soluble compound. Preferably the ruthenium solution is an aqueous ruthenium solution, preferably containing a ruthenium chloride, such as $RuCl_3$, or $Ru(NO)(NO_3)_3$. Ruthenium trichloride is most preferred.

The ruthenium is present on the $TiO_2$ support in a finely divided state. After the base treatment of this invention, the support surface is more uniformly covered by ruthenium than on a comparable catalyst prepared by saturating a $TiO_2$ support with a ruthenium solution to the point of incipient wetness, but not base treated according to the invention. That is, with base treatment the ruthenium disperses more evenly over the entire surface, so that a larger portion of the support is covered with smaller ruthenium crystallites and a greater fraction of ruthenium atoms are exposed to the reaction medium (i.e., the fraction of surface ruthenium atoms relative to total ruthenium atoms is higher for smaller crystallites).

The first step of the process comprises saturating a $TiO_2$ support with an aqueous ruthenium solution.

A preferred method for preparing the catalysts of the present invention is to first prepare an aqueous solution of a soluble ruthenium compound and then add this solution to the $TiO_2$ support such that the entire quantity of the solution is absorbed.

The first step of the process preferably comprises saturating a $TiO_2$ support with a ruthenium solution to the point of incipient wetness. By saturating the $TiO_2$ support to the point of "incipient wetness", reference is made to techniques described in U.S. Pat. No. 6,232,511 B1 and *Preparation of Catalyst*, Delmon, B., Jacobs, P. A., Poncald, G. (eds.), Amsterdam Elsevier, 1976, Page 13, whereby water or other solvent is applied in sufficient quantity to fill the pores. The process is preferably carried out so that the solution fills the support pores with little excess. To this end, the water absorption capacity of the support is determined. An aqueous ruthenium chloride solution is prepared which has a concentration corresponding to the subsequent ruthenium coating. The support is loaded with the aqueous ruthenium chloride solution in accordance with its water absorption capacity such that the entire quantity of the solution is absorbed. Then, the base treatment is carried out with the aqueous base solution. In the most preferred embodiment of the invention, the base treated ruthenium saturated support is subsequently cured, washed, dried and then heat treated under reducing conditions as described herein.

The base treatment is carried out so that the $TiO_2$ support is saturated with an aqueous solution containing ruthenium and base. The pH of the saturating solution can be measured using a pH strip or by other standard techniques (such as using a pH probe). The pH is preferably at least about 3, more preferably at least about 3.5, and is preferably up to about 12, more preferably up to about 7, and most preferably up to about 5. That is, the aqueous ruthenium solution is acidic, and by increasing the solution pH using base solution the ruthenium is better dispersed on the $TiO_2$ support because of the less acidic environment.

Preferred bases include single base solutions and/or solutions comprising a mixture of bases. The preferred bases include LiOH, NaOH, KOH, $Ca(OH)_2$, $Mg(OH)_2$, and $NH_4OH$, or mixtures thereof. NaOH is most preferred. The amount of base in the aqueous base solution is selected in order to create a solution saturating the $TiO_2$ support with a desirable pH.

The method of adding aqueous base solutions to the support can be by any technique generally known in the art including immersion, spraying, or the like. The aqueous base is preferably applied immediately after the ruthenium is applied, but it is possible to leave some time between the two steps.

The next step is curing. The aqueous ruthenium and aqueous base solutions are allowed to contact the support for a sufficient period of time for ruthenium crystallites to form and deposit on the support surface (i.e., the ruthenium crystallites precipitate out of solution onto the $TiO_2$ support surface). Once the $TiO_2$ support is saturated with the ruthenium solution, the ruthenium crystallites will begin to precipitate onto the support. The curing time should be sufficient to allow precipitation of the desired amount of ruthenium. Preferred curing times are 30 minutes—5 hours, and the time will vary based upon conditions such as the amount of ruthenium in the solution, base and base concentration, volume of catalyst being prepared, etc. Curing is usually carried out at ambient or near ambient conditions, but conditions can be varied. Curing techniques are well known in the art.

Preferably the next step is washing with water, preferably distilled, deionized water. This step removes chloride and/or other ions (e.g., potassium, sodium, etc.). When a ruthenium chloride is used, the ruthenium bearing support is preferably washed until free of chloride, preferably to less than 100 ppm residual chloride.

The catalyst is preferably dried at a temperature greater than 20° C. and preferably under 120° C. (higher temperatures can be used), more preferably under 100° C., and most preferably about 80° C. Drying is preferably carried out in an inert gas atmosphere, such as neon, helium, argon, nitrogen or air. The lower the temperature, the longer its takes to dry. The drying step is normally carried out at atmospheric pressure, but also can be conducted under pressure or vacuum.

Preferably the ruthenium impregnated $TiO_2$ is then heat treated under reducing conditions at temperatures of about 150 to about 800° C.

By "reducing conditions" reference is made to heating the ruthenium impregnated $TiO_2$ under conditions, that is a hydrogen or other reducing agent environment, in which the average ruthenium ion charge will decrease. Other suitable reducing agents include formaldehyde, hydrazine hydrate, hydroxylamine, sodium hypophosphite, sodium formate, glucose, acetaldehyde, sodium borohydride, etc. Gaseous hydrogen (with or without a diluent, such as $N_2$) is preferred. Reducing is preferably carried out at atmospheric pressure or a slightly elevated pressure (e.g, about 1 to about 2 atmospheres), and is preferably carried out at a hydrogen concentration of 1 to 100% as a mixture with nitrogen.

Preferably the heating is at a temperature of at least about 250° C., more preferably at least about 300° C., even more preferably about 350° C., more preferably at least about 400° C., and most preferably at least about 450° C. Preferably the heating is at a temperature of up to about 700° C., more preferably up to about 550° C. One aspect of the invention is the discovery that temperatures of at least about 300° C. are preferred, with temperatures about 500° C. providing even better results.

The heat treating is preferably carried out for a period of about 20 minutes to about 24 hours, or more.

This preparation provides a fine subdivision of the ruthenium on the catalyst carrier, with crystallite sizes generally from about 1 to about 5 nm as measured by transmission electron microscopy.

The ruthenium is disposed on the support in a quantity of from 0.1 to 20 weight %, preferably about 0.1 to 10 weight %, most preferably about 0.1 to 5 weight % relative to the weight of the titanium dioxide.

The invention provides a reduced ruthenium on $TiO_2$ catalyst that exhibits nanometer-sized ruthenium crystallites homogeneously separated over the $TiO_2$ surface with interparticle spacings between crystallites on a nanometer scale, as determined by transmission electron microscopy. Transmission electron microphotograps corresponding to a catalyst not of the invention and to three catalyst preparations within the intended scope of this invention are included in FIGS. 1, and FIGS. 2-4, respectively.

Figure 2:
FIG. 2 is a photomicrograph of a ruthenium/$TiO_2$ catalyst corresponding to example 1.
Figure 3:
FIG. 3 is a photomicrograph of a ruthenium/$TiO_2$ catalyst corresponding to example 2.
Figure 4:
FIG. 4 is a photomicrograph of a ruthenium/$TiO_2$ catalyst corresponding to example 4.

Preferably as a result of the base treatment, as can be seen from FIGS. 2-4, at least 10% more of the surface of the support is covered with the ruthenium than on the catalyst prepared without base treatment as shown in FIG. 1. The additional coverage is because the ruthenium is better dispersed as smaller crystallites.

The preferred catalyst comprises 0.1 to 20 weight % ruthenium crystallites, by weight of the catalyst, on a $TiO_2$ support. Preferably the Ru crystallites on the $TiO_2$ surface are, on average, about 10 nm or less. With base treatment the ruthenium disperses more evenly over the entire surface, so that a larger portion of the support is covered with smaller ruthenium crystallites and a greater fraction of ruthenium atoms are exposed to the reaction medium (i.e., the fraction of surface ruthenium atoms relative to total ruthenium atoms is higher for smaller crystallites).

The invention is further directed to use of the catalysts described above or prepared by the foregoing processes. Preferably the process is for the production of 1,3-propanediol (PDO), comprising (a) providing 3-hydroxypropanal (HPA) and the catalyst, and (b) hydrogenating the 3-hydroxypropanal in the presence of the catalyst. Preferably this process is carried out in aqueous solution at a pH value of 2.5 to 7, at temperatures of 30 to 180° C., at hydrogen pressure of 5 to 300 bar. Preferably the process produces a hydrogenation product stream containing less than 1 weight % 2-(2'-hydroxyethyl)-1,3-dioxane (as percent of organic materials) and 3-hydroxypropanol conversion to 1,3-propanediol of greater or equal to 90%, preferably at least 95% and more preferably at least 99%.

The HPA is reacted with hydrogen in the presence of the supported ruthenium catalyst using methods known in the art. For example, stirred reactors or flow reactors may be used. A fixed-bed hydrogenation reactor is particularly suitable for conducting the hydrogenation on an industrial scale. In such a reactor, the liquid reaction mixture flows or trickles over the fixed-bed catalyst together with the hydrogen introduced. To ensure good distribution of the hydrogen in the reaction mixture and uniform distribution of the gas/liquid mixture over the entire cross-section of the fixed bed, the liquid reaction mixture and hydrogen may be passed together through static mixers before the catalyst bed. Trickle bed reactors are particularly preferred and are described in Kirk-Othmer Encyclopedia of Chemical Technology, Third Edition (1982), Volume 19, pages 880-914 (especially page 884). A trickle bed reactor is preferred because it provides low liquid hold-up time, thus reducing the extent of side reactions such as acrolein formation from HPA resulting in a higher selectivity.

The HPA is generally fed to the reactor as an aqueous solution having a 3-hydroxypropanal concentration of between 2 and 18 weight % and a pH between 2.5 and 7. In continuous processes, liquid hourly space velocities between 0.1 and 10 $h^{-1}$ are preferred. The hydrogenation reaction is conducted at a temperature of from 30° C. to 180° C. at a hydrogen pressure of 5 to 300 bar, preferably at a hydrogen pressure of less than 90 bar, most preferably from 10 bars to 60 bars. It is an advantage of the current invention that high constant conversions are obtained at lower hydrogen pressures compared to other catalysts. For example, the titanium dioxide supported platinum catalysts of U.S. Pat. No. 5,364,984 generally require hydrogen pressures greater than about 90 bars to achieve high and constant conversion over the service life of the catalyst.

EXAMPLES

Titanium dioxide from two sources was used as supports for the catalysts of the present invention and comparative catalysts. Aeroxide® $TiO_2$ P25 (Degussa Corporation, Piscataway, N.J.) (P25 catalyst) was used in two forms: 1) as received (referred to as P25 in the Tables below), and 2) after calcination in air at 800° C. (referred to as P25-800) for 1-3 hours. X-ray diffraction analysis of these two $TiO_2$ supports showed rutile contents of 19 and 99% for P25 and P25-800, respectively. Anatase 99.9%, obtained from Aldrich (Milwaukee, Wis.), was used as obtained. Surface areas for P25, P25-800 and anatase were measured to be 52, 13.5 and 12.5 $m^2/g$, respectively.

Powdered catalysts were prepared according to the following method:
(1) The water absorption of the support was determined in g of $H_2O$ per g of support.
(2) $RuCl_3$ was dissolved in distilled water for loading 5 g of support.
(3) The $RuCl_3$ solution was added dropwise to the support while stirring to ensure uniform liquid distribution. The $TiO_2$ support was saturated with a ruthenium solution to the point of incipient wetness.
(4) When used, the desired amount of aqueous 20% NaOH solution was added dropwise to the wetted mixture and stirred to ensure uniform distribution.
(5) After allowing the mixture to cure for at least 3 hours, the ruthenium impregnated $TiO_2$ was washed with distilled water to a residual $Cl^-$ content below 100 ppm.
(6) The coated support was dried overnight at 80° C. (in vacuo) with a nitrogen purge.
(7) The catalyst was reduced with hydrogen at the temperatures described below for 4 hours followed by cooling in hydrogen until the catalyst reached room temperature.

Hydrogenations were carried out in a batch mode or performed continuously in a trickle bed apparatus (Kirk-Othmer Encyclopedia of Chemical Technology, Third Edition (1982), Volume 19, pages 880-914, especially page 884) having a reactor volume of 30 ml, as indicated below. The trickle bed apparatus consisted of a liquid vessel, the fixed bed reactor, and a liquid separator. The reaction temperature was adjusted by means of a heat transfer medium/oil circuit. The hydrogen stream was electronically controlled. The aqueous HPA solution was apportioned to the hydrogen stream with a pump and the mixture introduced into the top of the reactor (trickle bed operation). Once the mixture had passed through the reactor, the resultant product was removed from the separator at regular intervals. The hydrogenation temperature was 40° C., the hydrogen pressure 40 bar, and the liquid loading, LHSV, was 1.0 h$^{-1}$. The PDO concentration in the reaction product stream was measured by gas chromotography using a flame ionization detector and was used in calculating the reported conversions and selectivities. HED levels were also determined by gas chromatography and are reported as flame ionization detector (FID) area % of total organics present in the aqueous product stream.

Examples 1-7 and Comparative Examples 1-4

Catalyst Preparation

This example demonstrates the advantages of Ru/TiO$_2$ catalysts prepared using the base treatment of the invention.

The catalysts listed in Table 1, comparative examples 1-4 (labeled Comp ex 1) and Examples 1-7, were prepared by incipient wetness impregnation of Ru (from RuCl$_3$) to a nominal loading of 2% onto the TiO$_2$ powders, as described above. When used, 20% NaOH solution was added after Ru impregnation to reach the molar OH$^-$/Ru ratios specified in Table 1. The solution pH (pH of the solution on the support) was measured after preparation of selected catalysts. Following impregnation, catalysts were washed, dried and reduced in flowing H$_2$ at the specified temperatures.

TABLE 1

List of Powdered Ru/TiO$_2$, Catalysts (all nominally 2% Ru)

| Catalyst | Support | OH$^-$/Ru | pH[3] | Reduction T(° C.) |
|---|---|---|---|---|
| Comp ex 1 | P25[1] | 0 | NM[4] | 150 |
| Comp ex 2 | P25 | 0 | NM | 300 |
| Comp ex 3 | P25 | 0 | NM | 500 |
| Comp ex 4 | P25-800[2] | 0 | NM | 150 |
| Example 1 | P25-800 | 1.7 | NM | 150 |
| Example 2 | P25-800 | 2.8 | NM | 150 |
| Example 3 | P25-800 | 2.8 | NM | 300 |
| Example 4 | P25-800 | 2.8 | NM | 500 |
| Example 5 | P25-800 | 5.3 | 12 | 150 |
| Example 6 | Anatase | 2.0 | 3.5 | 150 |
| Example 7 | Anatase | 3.0 | 6.5 | 150 |

[1]Aeroxide ® TiO$_2$ P25 (Degussa Corporation, Piscataway, NJ)
[2]Aeroxide ® TiO$_2$ P25 (Degussa Corporation, Piscataway, NJ) calcined in air at 800° C.
[3]The pH of saturation solution on TiO$_2$ support.
[4]NM means not measured.

Electron microscopy can be used to elucidate the effect of caustic (NaOH) addition during catalyst preparation. The large 50-200 nm particles shown in FIGS. 1-4 are the TiO$_2$ support particles. The smaller 2-6 nm particles dispersed on the surface of the TiO$_2$ support particles are Ru crystallites. For the catalyst prepared without NaOH (comparative example 4, FIG. 1), Ru crystallites are observed to sparsely cover the TiO$_2$ support surface in some areas and to aggregate in other regions, resulting in poor dispersion of Ru. An increase in the addition of NaOH (Example 1, FIG. 2) results in less agglomeration of Ru crystallites or better coverage of the TiO$_2$ surface by Ru crystallites. As the NaOH is increased to the level used in preparing the catalyst of Example 2 (FIG. 3), sub-10 nm Ru crystallites on the TiO$_2$ surface are observed to be more evenly distributed over the support surface and consequently provide higher activity for the same metal loading. Reduction at 500° C. alone (the catalyst of Example 4, FIG. 4) does not significantly alter the distribution of Ru crystallites over the TiO$_2$ surface.

The performance of the catalysts prepared in Examples 1-2 and 5-7 were compared with those of Comparative Examples 1-2 in the following example.

Examples 8-12 and Comparative Examples 5-6

PDO Preparation

PDO was prepared by hydrogenation of 7 grams of an aqueous solution having a pH of 4 containing approximately 10% HPA with 0.2 g of the selected catalysts (prepared according to the procedures described above) in batch reactors solution at 40° C. and 600 psi for 25 minutes. Samples of the product solution were measured immediately after completion of the reactions to analyze for conversion to PDO and formation of byproducts, in particular HED. Table 2 lists the conversions and selectivities for Ru/TiO$_2$ catalysts compared to those obtained with a reference 5% Ru/SiO$_2$ catalyst (a crushed and reduced sample of the catalyst used in Examples B3 and B4 of U.S. Pat. No. 6,232,511 B1). Results of batch tests listed in Table 2 below show the amount of PDO formed relative to the amount formed with the reference catalyst (i.e., a relative PDO formation of 1 indicates the conversion to PDO for a given catalyst to be comparable to that of the reference catalyst). The last column lists the selectivity to PDO of the specified catalyst relative to the selectivity to PDO of the reference catalyst (i.e., a relative selectivity of 1 indicates that the specified catalyst has the same selectivity to PDO as the reference catalyst).

TABLE 2

Effect of Caustic Addition on Catalytic Activity and Selectivity

| Ex. No. | Catalyst | Support | OH$^-$/Ru (pH) | Relative PDO Formation | Relative Selectivity to PDO |
|---|---|---|---|---|---|
| Comp ex 5 | Comp ex 1 | P25 | 0 | 0.39 | 0.58 |
| Comp ex 6 | Comp ex 4 | P25-800 | 0 | 0.77 | 0.73 |
| 8 | Ex 1 | P25-800 | 1.7 | 1.18 | 1.19 |
| 9 | Ex 2 | P25-800 | 2.8 | 1.28 | 1.28 |
| 10 | Ex 5 | P25-800 | 5.3 (12) | 1.65 | 1.29 |
| 11 | Ex 6 | anatase | 2.0 (3.5) | 1.78 | 1.21 |
| 12 | Ex 7 | anatase | 3.0 (6.5) | 1.62 | 1.24 |

Addition of caustic (NaOH) during preparation resulted in a marked increase in activity and selectivity. The enhanced activity associated with caustic addition pertains both to rutile and anatase TiO$_2$.

Examples 13-16 and Comparative Examples 7-9

Reduction Temperature

These examples demonstrate the benefits of reduction treatment according to the preferred embodiment of this invention.

For comparative examples 7 and 9, the catalysts tested consisted of 2% Ru impregnated onto P25 and P25-800 as described above with respect to comparative example 1 and example 2, respectively.

Comparative examples 8 and example 14 employed the same catalysts as comparative example 7 and example 13, respectively; however, after preparation, the catalysts were reduced in H$_2$ at 300° C. prior to testing.

Comparative example 9 and example 15 also used these same 2 catalysts, but the catalysts were reduced in hydrogen at 500° C. prior to use. Because the exact duration of batch tests varied due to differences in heating and cooling of samples, all batch tests were performed simultaneously with testing of a reference 2% Ru/TiO$_2$ catalyst, whose activity was determined to be similar to that of the reference 5% Ru/SiO$_2$ catalyst used previously. Results of batch tests reported in Table 3 have been adjusted to show amounts of PDO formed and selectivities to PDO for specified catalysts relative to the reference 5% Ru/SiO$_2$ catalyst.

TABLE 3

Effect of Hydrogen Treatment Temperature

| Ex. No. | Catalyst | Support | OH$^-$/Ru | Reduction Temp. (° C.) | Relative PDO Formation | Relative Selectivity to PDO |
|---|---|---|---|---|---|---|
| Comp ex 7 | Comp ex 1 | P25 | 0 | 150 | 0.39 | 0.58 |
| Comp ex 8 | Comp ex 2 | P25 | 0 | 300 | 0.60 | 0.74 |
| Comp ex 9 | Comp ex 3 | P25 | 0 | 500 | 0.45 | 2.11 |
| 13 | Ex 2 | P25-800 | 2.8 | 150 | 1.28 | 1.28 |
| 14 | Ex 3 | P25-800 | 2.8 | 300 | 1.95 | 1.28 |
| 15 | Ex 4 | P25-800 | 2.8 | 500 | 1.25 | 1.52 |

The 2% Ru/P25 catalyst reduced at 150° C., shown in comparative example 7, exhibits lower levels of PDO formation than the reference catalyst and low selectivity to PDO. The low selectivity is due to the high levels of HED formed using this catalyst. Increasing the reduction temperature to 300° C., as shown in comparative example 8, results in an increase in both activity and selectivity. Still, the selectivity is low due to the formation of significant levels of HED. For the catalyst reduced at 500° C., as shown in comparative example 9, the selectivity to PDO increases to higher than that of the reference catalyst due to very low levels of HED formation; however, the activity is lower as reflected by a low Relative PDO Formation.

Batch testing of the 2% Ru/P25-800 catalyst prepared with base treatment and reduced at 150° C., as shown in Example 13, shows that this catalyst's activity and selectivity towards PDO formation are slightly better than those of the reference catalyst. Increasing the reduction temperature to 300° C., as performed in Example 14, results in an improvement in PDO formation rate, but does not affect catalyst selectivity to PDO. In contrast, when the reduction temperature is further increased to 500° C., as shown in Example 15, catalytic activity is the same as for the catalyst reduced at 150° C., but catalyst selectivity to PDO increases significantly. Analysis of the products formed reveal that this is due to a significant decrease in the formation of HED. This decrease in HED formation as a function of reduction temperature occurs even for the less active 2% Ru/P25 catalyst. Therefore, increasing the hydrogen treatment temperature significantly improves catalyst selectivity without impairing catalyst activity.

Examples 16-18 and Comparative Examples 10-11

A series of 0.5% Ru/TiO$_2$ fixed bed catalysts were prepared. These catalysts were prepared on a P25 support. Ru was deposited in a thin layer on the surface of the catalyst pellets, otherwise known as surface-loaded or an "eggshell" catalyst (as referenced in Johnson Matthey Heterogeneous Catalysis Technical Guide, p. 4, or Degussa Fixed Bed Catalysts brochure, p. 2). Table 4 lists the preparation conditions for these catalysts.

TABLE 4

List of Edge-Coated 0.5% Ru/TiO$_2$ Fixed Bed Catalyst (all prepared using fixed bed P25 catalyst support)

| Catalyst | OH$^-$/Ru | pH | Reduction T (° C.) |
|---|---|---|---|
| Comp ex 10 | 0 | NM* | 200 |
| Example 16 | NM | 6 | 200 |
| Comp ex 11 | 0 | NM | 500 |
| Example 17 | NM | 6 | 500 |
| Example 18 | NM | 6 | 400 |

*NM means not measured.

A pH of 6 indicates the use of base treatment whereas the reference to 0 OH$^-$/Ru indicates that base treatment was not conducted. These catalysts were used in the following examples.

Examples 19-21 and Comparative Example 12-13

PDO Preparation

Comparative example 12 was performed using the catalyst of comparative example 10. Continuous operation was performed in a fixed bed reactor by flowing a 10% aqueous HPA solution, having a pH of 4, at a temperature of 40° C. and a H$_2$ pressure of 600 psi. The level of HED measured in the product of the first sample is listed in Table 5. Rates of PDO formation as a function of time are also listed in Table 5.

Examples 19-21 were performed using the catalysts of Examples 16-18, respectively. Continuous testing was performed in the same manner as in Comparative Example 12. Results are tabulated in Table 5.

TABLE 5

Effect of NaOH Treatment and Reduction Temperature on Performance of 0.5% Ru/TiO$_2$ Fixed Bed Catalysts

|  | Comp ex 12 | Example 19 | Comp ex 13 | Example 20 | Example 21 |
|---|---|---|---|---|---|
| Catalyst | Comp ex 10 | Example 16 | Comp ex 11 | Example 17 | Example 18 |
| Reduction T (° C.) | 200 | 200 | 500 | 500 | 400 |
| NaOH Treat. | No | Yes | No | Yes | Yes |
| HED in 1$^{st}$ Sample | 1.9 | 0.2 | not detected | not detected | 0.5 |

TABLE 5-continued

Effect of NaOH Treatment and Reduction Temperature on Performance of 0.5% Ru/TiO$_2$ Fixed Bed Catalysts

| Rates in kg PDO/L/h | Time (h) | Rate | Time (h) | Rate | Time (h) | Rate | Time (h) | Rate | Time (h) | Rate |
|---|---|---|---|---|---|---|---|---|---|---|
| | 2 | 0.083 | 17 | 0.051 | 3 | 0.105 | 5 | 0.084 | 3 | 0.077 |
| | 18 | 0.016 | 27 | 0.022 | 22 | 0.058 | 21 | 0.062 | 18 | 0.076 |
| | 42 | 0.007 | 35 | 0.026 | 46 | 0.040 | 47 | 0.049 | 42 | 0.054 |
| | | | 54 | 0.023 | 53 | 0.037 | 70 | 0.040 | 67 | 0.043 |
| | | | 78 | 0.020 | | | 78 | 0.038 | | |

Comparison of the results of Comparative Example 12 with the results of Comp ex 13 shows the decreased formation of HED caused by the higher catalyst reduction temperature. Furthermore, an enhanced activity and lifetime behavior is observed as a consequence of the higher temperature of reduction.

Comparison of the results of Comparative Example 12 with Example 19 illustrates the improvement in HED formation and lifetime performance as a consequence of NaOH treatment.

Comparison of the results of Example 19 with Examples 20 and 21 illustrate the improvement in lifetime performance as a consequence of the higher temperature of reduction. In all three examples, favorably low levels of HED are produced.

What is claimed is:

1. A process for preparing a catalyst, comprising sequentially: (a) saturating a TiO$_2$ support with aqueous ruthenium solution; and (b) treating the ruthenium saturated TiO$_2$ support with an aqueous base solution and (c) curing the ruthenium saturated TiO$_2$ to impregnate the TiO$_2$ with ruthenium, wherein subsequent to step (c) the process comprises heat treating the ruthenium impregnated TiO$_2$ under reducing conditions at temperatures 150-800° C., such that the resulting catalyst comprises 0.1 to 20 weight% ruthenium crystallites present on the TiO$_2$ support in a finely divide state.

2. The process of claim 1, wherein subsequent to step (c) the process comprises sequentially (d) washing the ruthenium impregnated TiO$_2$ with water, (e) drying the washed ruthenium impregnated TiO$_2$, and (f) heat treating the ruthenium impregnated TiO$_2$ under reducing conditions at temperatures of 150-800° C.

3. The process of claim 2, wherein the heat treating is carried out for a period of 20 minutes to 24 hours at a temperature of about 300-about 550° C. at a hydrogen concentration of 1 to 100% as a mixture with nitrogen.

4. The process of claim 2, wherein the ruthenium solution is an aqueous ruthenium solution containing RuCl$_3$ or Ru(NO)(NO$_3$)$_3$.

5. The process of claim 2, wherein after the treating step (b) the TiO$_2$ is saturated with an aqueous solution comprising ruthenium and base having a pH of at least about 3.

6. The process of claim 2, wherein the pH is at least 3.5.

7. The process of claim 2, wherein the pH is up to about 12.

8. The process of claim 2, wherein the pH is up to about 7.

9. The process of claim 2, wherein the pH is up to about 5.

10. The process of claim 2, wherein the saturating a TiO$_2$ support with ruthenium solution is carried out to the point of incipient wetness.

11. The process of claim 2, wherein the base is selected from the group consisting of LiOH, NaOH, KOH, Ca(OH)$_2$, Mg(OH)$_2$, and NH$_4$OH, or mixtures thereof.

12. The process of claim 2, wherein the base is selected from the group consisting of LiOH, NaOH, KOH, Ca(OH)$_2$, Mg(OH)$_2$, and NH$_4$OH.

13. The process of claim 2, wherein the base is NaOH.

14. The process of claim 2, wherein the drying is carried out at a temperature of 20 to 120° C. in an inert gas.

15. The process of claim 2, wherein the catalyst consists essentially of 0.1 to 20 weight % of the ruthenium, by weight of the catalyst.

16. The process of claim 1, wherein the ruthenium solution is an aqueous ruthenium solution containing RuCl$_3$ or Ru(NO)(NO$_3$)$_3$.

17. The process of claim 1, wherein the heat treating is at a temperature of at least about 250° C.

* * * * *